United States Patent [19]
Wamsiedler et al.

[11] Patent Number: 6,042,784
[45] Date of Patent: Mar. 28, 2000

[54] METHOD AND APPARATUS FOR ULTRAFILTRATION IN HEMODIALYSIS

[75] Inventors: Ralf Wamsiedler, Schonungen; Raimund Walter, Schwebheim, both of Germany

[73] Assignee: Fresenius Medical Care Deutschland GmbH, Bad Homburg, v.d.H., Germany

[21] Appl. No.: 09/032,645

[22] Filed: Feb. 27, 1998

[30] Foreign Application Priority Data

Mar. 1, 1997 [DE] Germany .......................... 197 08 391

[51] Int. Cl.[7] ............................. A61M 37/00; A61M 1/14
[52] U.S. Cl. ............................................. 422/44; 604/4
[58] Field of Search ...................... 210/741, 646; 604/4, 5; 422/44

[56] References Cited

U.S. PATENT DOCUMENTS

| | | | |
|---|---|---|---|
| 4,209,391 | 6/1980 | Lipps et al. | 210/22 |
| 4,267,040 | 5/1981 | Schal | 210/104 |
| 4,770,769 | 9/1988 | Schael | 210/96.2 |
| 5,092,836 | 3/1992 | Polaschegg | 604/4 |
| 5,151,082 | 9/1992 | Gorsuch et al. | 604/4 |
| 5,336,165 | 8/1994 | Twardowski | 604/5 |
| 5,344,568 | 9/1994 | Kitaevich et al. | 210/645 |
| 5,536,412 | 7/1996 | Ash | 210/646 |
| 5,725,776 | 3/1998 | Kenley et al. | 210/646 |
| 5,792,367 | 8/1998 | Mattisson et al. | 210/741 |

FOREIGN PATENT DOCUMENTS

| | | |
|---|---|---|
| 28 38 414 C2 | 3/1980 | Germany . |
| 38 37 498 C2 | 5/1990 | Germany . |
| 41 16 178C1 | 11/1992 | Germany . |

Primary Examiner—Ronald Stright
Assistant Examiner—Cheryl L. Huseman
Attorney, Agent, or Firm—Kenyon & Kenyon

[57] ABSTRACT

A method and device for accurately determining the volume of and replacing ultrafiltrate in hemodiafiltration using an ultrafiltrate balance chamber that is subdivided by a movable partition into two balance chamber halves. The two balance-chamber halves being alternately filled, one with ultrafiltrate and the other with substituate, such that the volume of ultrafiltrate is balanced against the volume of substituate. The filling of one chamber with ultrafiltrate or substituate displaces an equal volume of substituate or ultrafiltrate from the other chamber half and diverts the displaced ultrafiltrate or substituate from the balance chamber. The filling volume of the ultrafiltrate balance chamber is used to determine the ultrafiltrate volume or the volume of substituate.

21 Claims, 4 Drawing Sheets

METHOD AND APPARATUS FOR ULTRAFILTRATION IN HEMODIALYSIS

FIELD OF THE INVENTION

The present invention relates to a method of ultrafiltration in hemodialysis and an apparatus for carrying out the method.

BACKGROUND OF THE INVENTION

In treating chronic renal failure, various methods of purification and treatment of blood with machinery are used for removing substances usually eliminated with the urine and for withdrawing fluids. Diffuse mass transport is predominant in hemodialysis (HD), but in hemofiltration (HF) convective mass transport through a membrane is used. Hemodiafiltration (HDF) is a combination of the two methods.

Because of the large exchange volumes, there is a need in these methods for accurate balancing of fluid withdrawn relative to fluid administered and the volume for ultrafiltration over the entire treatment time. Gravimetric and volumetric balancing systems are state of the art.

German Patent DE-PS 2,838,414 discloses a dialysis device having a volumetric balancing device. The balancing device consists of two chambers subdivided by a displaceable element and each having an inlet line for fresh dialysis fluid and an outlet line connected to a drain for spent dialysis fluid. Cutoff valves driven and switched by a control unit are arranged in the inlet and outlet lines. A pump is provided between the dialyzer and the balancing device to convey the spent dialysis fluid. In addition, a dialyzer valve is provided in the inlet line to the dialyzer, and an air separator is provided in the outlet line.

The known device is operated in such a way that fresh dialysis fluid is supplied from a dialysis fluid source to the two balancing chambers in alternation through appropriate switching of the cutoff valves in the inlet lines. At the same time, fresh dialysis fluid is supplied from an already filled space of the other balance chamber to the dialyzer, where the desired toxins are removed by diffusion from the blood which is also flowing through the dialyzer. The spent dialysis fluid is then pumped into the second space of the same balance chamber, from which the spent dialysis fluid then goes into an outlet.

The part of the liquid circuit enclosed between the balancing device and the dialyzer behaves like a closed, constant-volume system. A tapping device is provided to remove liquid from this system.

On the basis of the above-mentioned properties of the balancing device, the volume of fluid removed from the system by the tapping device is replaced by an equally large volume of fluid which goes from the blood side to the dialysis fluid side of the dialyzer membrane. The volume of fluid removed can be supplied to the patient again as replacement fluid. However, 1:1 replacement of the volume of fluid removed is not absolutely essential. Instead, it may be advantageous in individual cases to remove a larger volume of fluid than the volume of replacement fluid administered to the patient, i.e., despite replacement there may be a net ultrafiltration.

High demands are to be made on the accuracy of the tapping device, permitting control of ultrafiltration. To be able to withdraw a precisely predeterminable volume of ultrafiltrate from the dialysis fluid path, the tapping device is equipped with a volumetric diaphragm pump, with each individual pump stroke corresponding to a unit volume of ultrafiltrate. One disadvantage is that a separate pump with a relatively complicated design is necessary for removing a precisely predeterminable volume of ultrafiltrate.

German Patent DE 3,837,498 C2 describes a device where ultrafiltration is performed without an additional ultrafiltrate pump. The ultrafiltrate is not removed through a separate tapping device in the dialysis fluid path between the dialyzer outlet and the balancing device, but instead is removed in a controlled manner from the dialysis fluid path via the balancing device, with the dialysis fluid path being interrupted between two hemodialysis cycles. The balancing device of the known apparatus has two balance chambers. When ultrafiltrate flows into a first balance-chamber half of a first of the two balance chambers, fresh dialysis fluid from the second half of the first balance-chamber into either of a first or a second balance chamber half in the second balance chamber.

In addition, there is a device for ultrafiltration in dialysis, where the quantity of ultrafiltrate is determined by means of a balance chamber. The balance chamber is subdivided by a flexible partition into two chamber halves which are alternately filled with the ultrafiltrate tapped from the dialysis fluid path, with the contents of the other half of the chamber being diverted. However, it is impossible with the known device to balance ultrafiltrate against substituate.

A hemofiltration device where ultrafiltrate is balanced against substituate by means of a balance chamber is known from German Patent DE 4,116,178 C1.

OBJECT OF THE INVENTION

An object of the present invention is to create a method of ultrafiltration in hemodialysis which will permit accurate balancing of ultrafiltrate against substituate without requiring a volumetrically precise ultrafiltration pump. Another object of the present invention is to provide a device for carrying out this method.

The present invention therefore provides a method of ultrafiltration in hemodialysis, where blood is sent in an extracorporeal blood circulation through the blood chamber of a dialyzer which is subdivided by a semipermeable membrane into a blood chamber and a dialysis fluid chamber. Dialysis fluid is sent through the dialysis fluid chamber of the dialyzer in a dialysis fluid path, and ultrafiltrate is removed from the dialysis fluid path. The fresh dialysis fluid flowing into the dialysis fluid chamber and the spent dialysis fluid flowing out of the dialysis fluid chamber are balanced in a dialysis fluid balancing device having at least one balance chamber subdivided by a movable partition into two balance-chamber halves. The method is characterized in that spent dialysis fluid in a first cycle is sent to into a balance-chamber of an ultrafiltrate balancing device, the balance chamber being subdivided by a movable partition into first and second balance-chamber halves, the spent dialysis fluid flowing into the first balance chamber half and thereby diverting substituate from the second balance chamber half. In a second cycle, substituate is sent into the second balance-chamber half, thereby diverting the spent dialysis fluid from the first balance-chamber half.

The present invention also provides an apparatus for carrying out this method having a dialyzer that is subdivided by a semipermeable membrane into a blood chamber and a dialysis fluid chamber, with the blood chamber being part of an extracorporeal blood circulation, a dialysis fluid source, inlet and outlet lines for supplying fresh dialysis fluid from the dialysis fluid source into the dialysis fluid chamber of the dialyzer and for removing spent dialysis fluid from the dialysis fluid chamber into a drain, a dialysis fluid balancing device connected to the inlet and outlet lines for balancing fresh and spent dialysis fluid, said device having at least one balance chamber which is subdivided into two balance-chamber halves by a movable partition, with cutoff elements arranged in the inlet and outlet lines of the balance-chamber halves, a control unit connected to the cutoff elements of the dialysis fluid balancing device, a device for removing ultrafiltrate from the dialysis fluid path, and a substituate source for supplying substituate. The apparatus is characterized in that the device for removing ultrafiltrate has an ultrafiltrate balancing device with a balance chamber subdivided by a movable partition into two balance-chamber halves, where the one chamber half is connected by a filtrate inlet line to the dialysis fluid path and by a filtrate outlet line to the drain, and the other chamber half of the balance chamber of the ultrafiltrate balancing device is connected by a substituate inlet line to the substituate source and is also connected to a substituate outlet line. Cutoff elements connected to the control unit are arranged in the filtrate and substituate lines, and the control unit is designed so that in a first cycle, one balance-chamber half of the balance chamber of the ultrafiltrate balancing device can be filled with spent dialysis fluid, diverting substituate from the other balance-chamber half, and in a second cycle, the other balance-chamber half can be filled with substituate, diverting the spent dialysis fluid from the one balance-chamber half.

In the method of ultrafiltration during hemodialysis according to the present invention, the ultrafiltration volume is determined using a balance chamber of an ultrafiltrate balancing device which is subdivided by a displaceable membrane into two balance-chamber halves. A volumetrically precise ultrafiltration pump is not necessary in the method according to the present invention.

The two balance-chamber halves of the balance chamber of the ultrafiltrate balancing device are alternately filled with spent dialysis fluid and substituate, with the contents of the other half of the chamber being diverted. In a first cycle, one chamber half is filled with spent dialysis fluid which is tapped from the dialysis fluid path, while the substituate previously sent into the other chamber is diverted. Then in a second cycle, the other chamber half is filled with substituate while the spent dialysis fluid is diverted. The filling volume of the balance chamber is used to determine the ultrafiltration volume or the substituate volume.

If the substituate diverted from the one chamber half is supplied to the blood circulation during the entire treatment period, a 1:1 balancing takes place, i.e., the patient is neither ultrafiltered nor hyperhydrated. However, the volume of ultrafiltrate removed from the dialysis fluid path may also be greater than the volume of substituate supplied to the blood circulation. In this case, the substituate diverted from the one chamber half is not added to the blood circulation during the entire treatment period or even just in individual cycles, but instead is supplied back to the substituate source or simply sent to an outlet. An accurate control of the net ultrafiltration volume over the entire period of dialysis is possible through alternating operation in these two modes.

The substitution fluid can either be supplied separately or obtained from the dialysis fluid (on-line HDF). Fresh dialysis fluid is preferably sent as substituate into the other balance-chamber half of the balance chamber of the ultrafiltrate balancing device. If the substitution fluid is not obtained from the dialysis fluid, an external device is necessary to supply the substitution fluid, either pumping the substituate or conveying it by using gravity. However, no high demands need be made on such a pump with regard to accuracy of delivery.

The fresh dialysis fluid is preferably balanced against the spent dialysis fluid in a dialysis fluid balancing device having two balance chambers connected in parallel and operating in alternation.

It is advantageous for the balance chamber of the ultrafiltrate balancing device to be capable of being driven via the balance chambers of the dialysis fluid balancing device. The cutoff elements arranged in the inlet lines and outlet lines of the balance chamber of the ultrafiltrate balancing device are preferably driven in the same cycle as the cutoff elements of the dialysis fluid balancing device.

BRIEF DESCRIPTION OF THE DRAWINGS

Examples of forms of embodiments of the present invention are explained in greater detail below on the basis of the drawings, in which.

DETAILED DESCRIPTION

Figure 1:
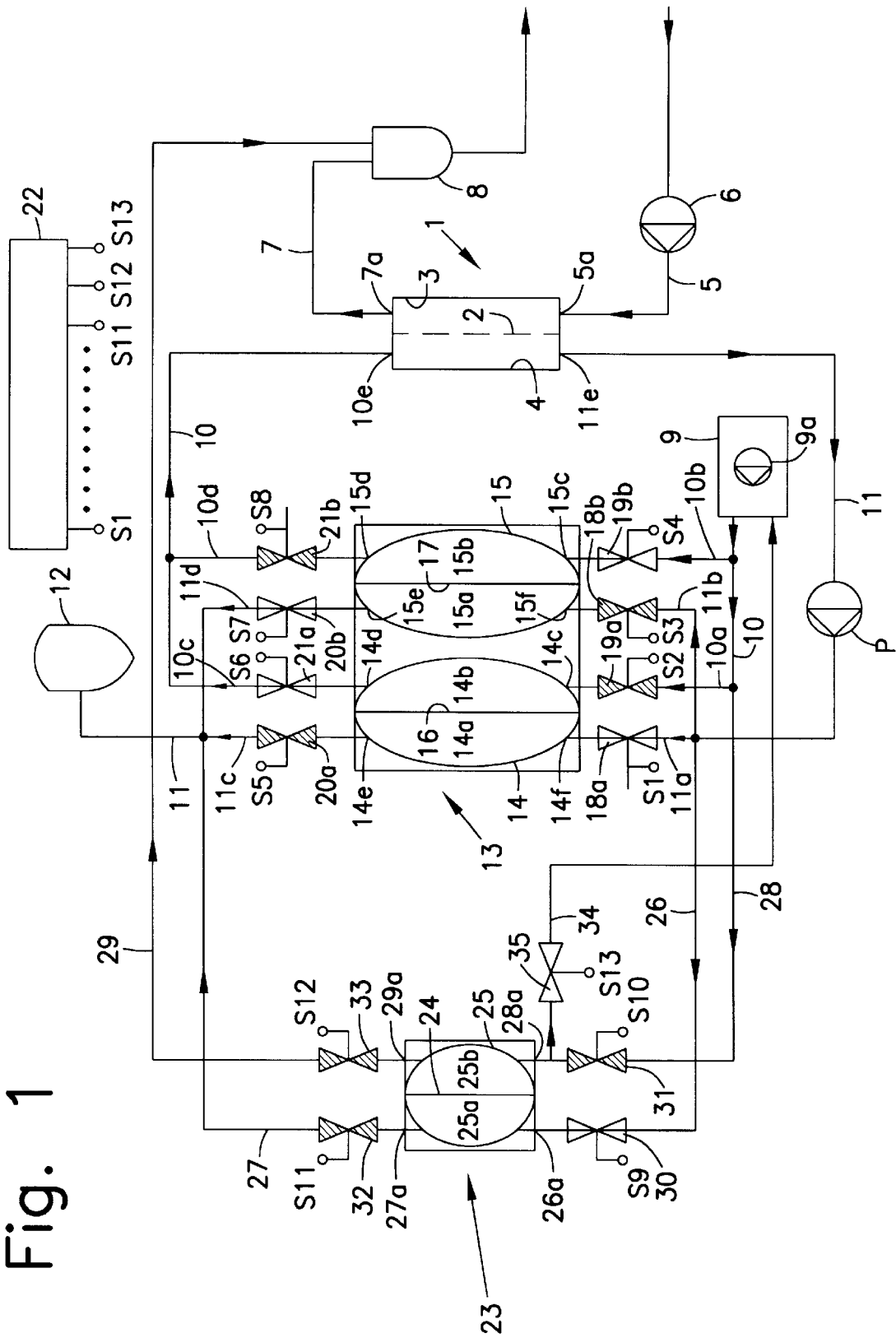
FIG. 1 shows a simplified schematic diagram of a preferred form of embodiment of the hemodiafiltration device, showing the open and closed positions of the cutoff elements of the balance chambers in the ultrafiltration mode during a first cycle.

FIG. 1 shows a simplified schematic diagram of a preferred form of embodiment of the hemodiafiltration device. The hemodiafiltration device has a dialyzer 1 which is subdivided by a semipermeable membrane 2 into a blood chamber 3 and a dialysis fluid chamber 4. To the inlet 5a of blood chamber 3 is connected a blood inlet line 5 which is also connected to a blood pump 6. Downstream from blood chamber 3, a blood outlet line 7 leads from the outlet 7a of the blood chamber to the patient. A drip chamber 8 is connected to the blood outlet line 7.

Fresh dialysis fluid is supplied from a dialysis fluid source 9 which has a degassing pump 9a. A dialysis fluid inlet line 10 leads from dialysis fluid source 9 to the inlet of the dialysis fluid chamber 4 of dialyzer 1, while a dialysis fluid outlet line 11 leads from the outlet of dialysis fluid chamber 4 to a drain 12. For balancing the dialysis fluid, a dialysis fluid balancing unit 13 is connected in the dialysis fluid inlet line 10 and outlet line 11. A dialysis fluid pump P is connected to the dialysis fluid outlet line 11 downstream from dialyzer 4.

The dialysis fluid balancing unit 13 has two balance chambers 14, 15, each having the same filling volume and subdivided by a movable partition 16, 17, e.g., in the form of a flexible membrane, into a first balance-chamber half 14a, 15a and a second balance-chamber half 14b, 15b, respectively. In this embodiment, each of the two balance chambers 14, 15 has a filling volume of 30 mL.

The part of the dialysis fluid inlet line 10 leading to the dialysis fluid balancing device 13 is divided into two line branches 10a, 10b, with one line branch 10a leading to the inlet 14c of the second chamber half 14b of the first balance chamber 14 and the other line branch 10b leading to the inlet 15c of the second chamber half 15b of the second balance chamber 15, with the part of the dialysis fluid inlet line 10 which leads away from balancing device 13 having two line branches 10c, 10d, with the one line branch 10c connected to the outlet 14d of the second chamber half 14b of the first balance chamber 14 and the other line branch 10d connected to the outlet 15d of the second chamber half 15b of the second balance chamber 15.

The part of dialysis fluid outlet line 11 leading to dialysis fluid balancing device 13 is also divided into two line sections 11a, 11b, with the one line section 11a being connected to the inlet 14f of the first chamber half 14a of the first balance chamber 14 and the other line section 11b being connected to the inlet 15f of the first chamber half 15a of the second balance chamber 15. The outlet 14c of the first chamber half 14a of the first balance chamber 14 is connected to drain 12 through line branch 11c, and the outlet of the first chamber half 15a of the second balance chamber 15 is connected to drain 12 through line branch 11d of dialysis fluid outlet line 11. Cutoff elements in the form of electromagnetically operated valves 18a, 18b, 19a, 19b, 20a, 20b and 21a, 21b are provided in the individual lines 10a through 10d and 11a through 11d and are connected to a central control unit 22 through control lines $S_1$ through $S_8$.

In addition to the dialysis fluid balancing device 13, the hemodiafiltration device also comprises an ultrafiltration balancing device 23 which has a balance chamber 25 subdivided by a movable partition 24, e.g., a flexible membrane, into two balance-chamber halves 25a, 25b. The balance chamber 25 has a filling volume of 6 mL in this embodiment example.

Upstream from valves 18a, 18b, a filtrate inlet line 26 branches off from the part of dialysis fluid line 11 leading to the dialysis fluid balancing device 13 and opens into the inlet 26a of the first chamber half 25a of balance chamber 25 of ultrafiltration balancing device 23, while the outlet 27a of the first chamber half 25a is connected to drain 12 over a filtrate outlet line 27 which connects to dialysis fluid outlet line 11. The inlet 28a of the second chamber half 25b is connected to dialysis fluid source 9 via a substituate inlet line 28 upstream from valves 19a, 19b. A substituate outlet line 29 leads from the outlet 29a of the second chamber half 25b into the drip chamber 8 arranged in blood outlet line 7 (postdilution). As an alternative, however, the substituate may also be supplied into a drip chamber arranged upstream from the dialyzer (predilution).

Additional cutoff elements in the form of electromagnetically operated valves 30, 31, 32, 33 are arranged in the filtrate inlet and outlet lines and the substituate inlet and outlet lines and are connected to the central control unit 22 via additional control lines $S_9$ through $S_{12}$. Downstream from valve 31, a drain line 34 branches off from substituate inlet line 28 and leads to dialysis fluid source 9. Another cutoff element 35 is arranged in drain line 34 and is connected by another control line $S_{13}$ to central control unit 22.

The required sterility of the dialysis fluid and the replacement fluid in particular can be guaranteed by installing known sterile filters (not shown for the sake of simplicity) in the fluid system.

Figure 2:
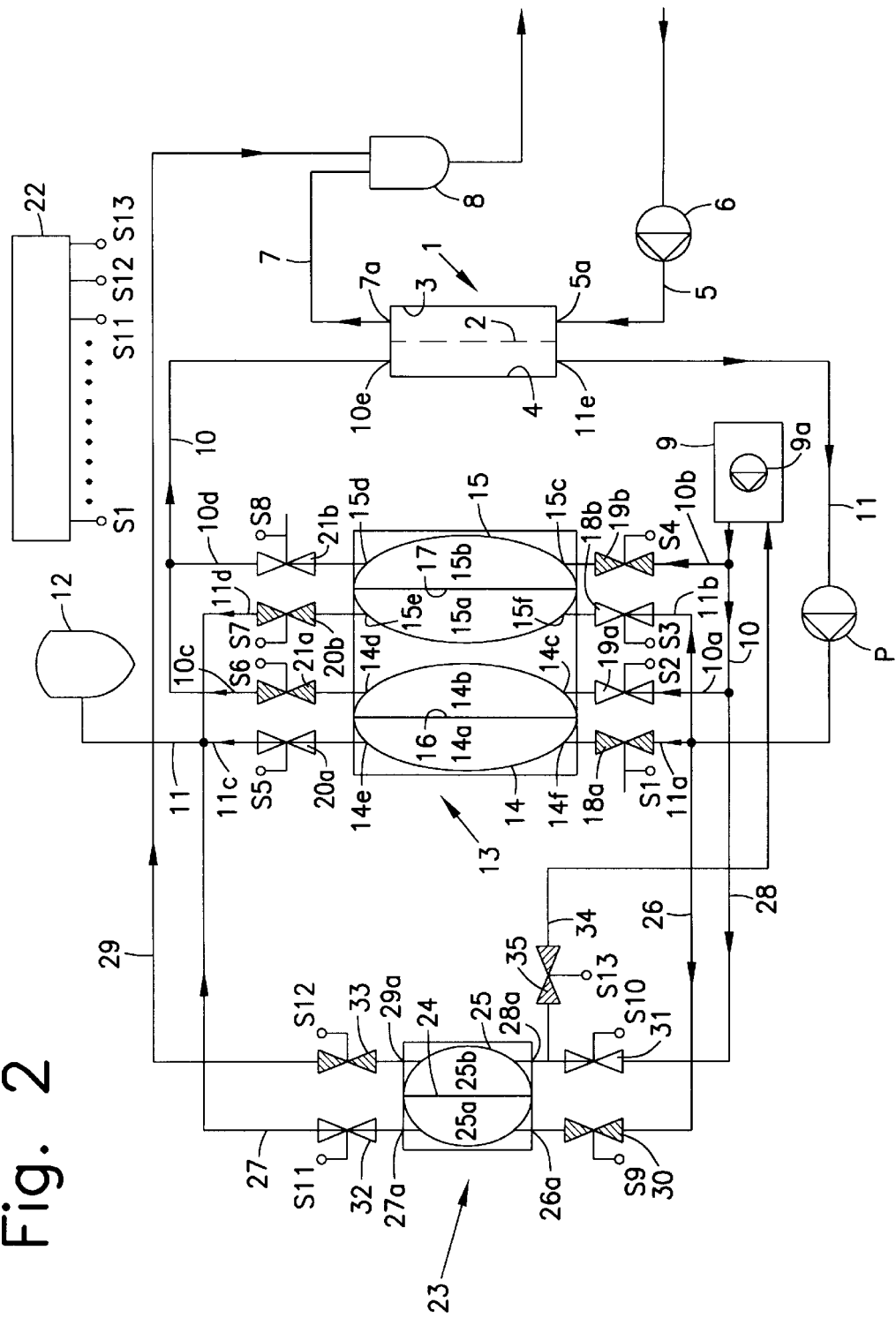
FIG. 2 shows the hemodiafiltration device of FIG. 1 in the ultrafiltration mode during a second cycle.
Figure 3:
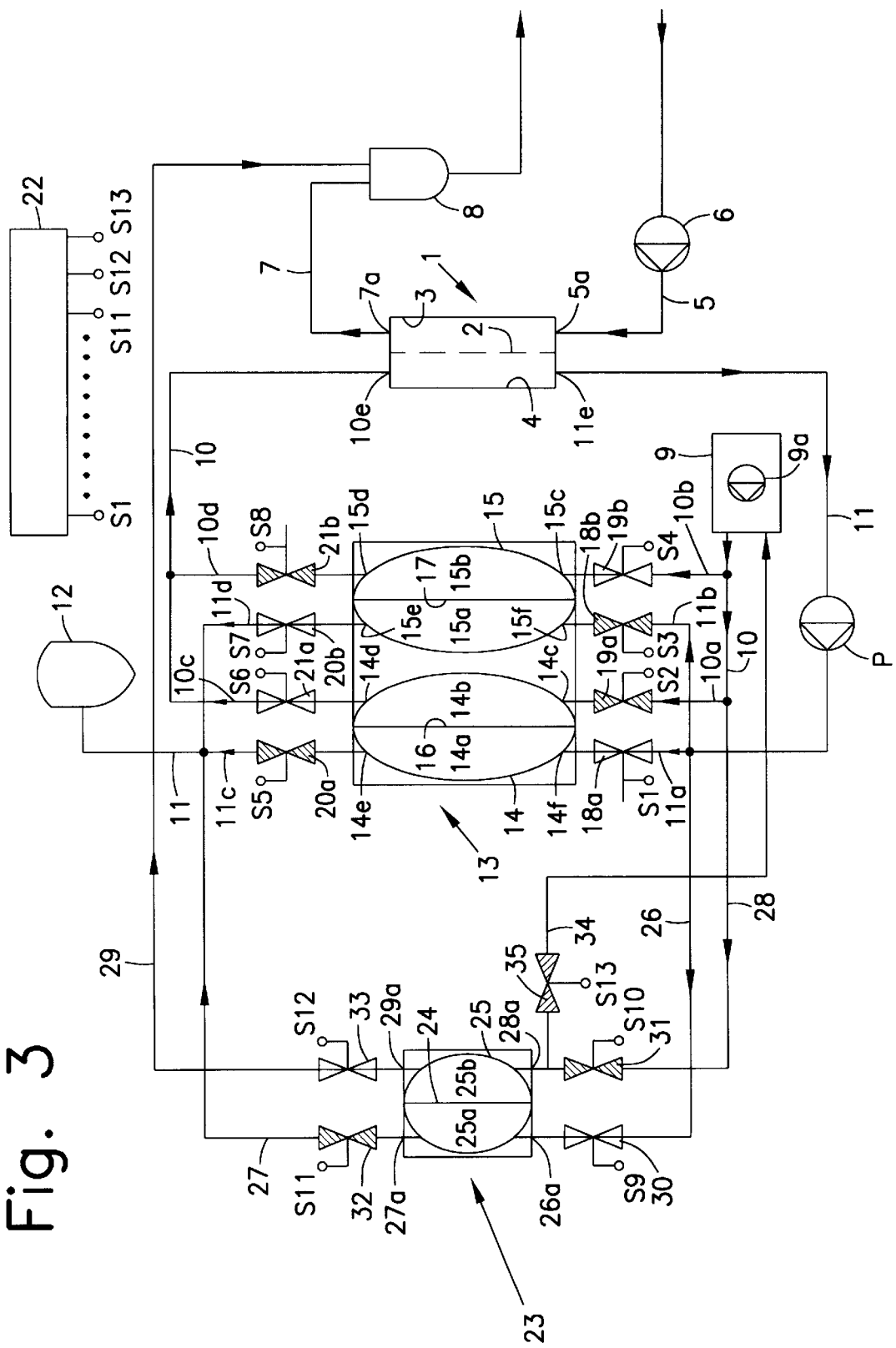
FIG. 3 shows the hemodiafiltration device of FIG. 1, showing the open and closed positions of the cutoff elements in the substitution mode during a first cycle.
Figure 4:
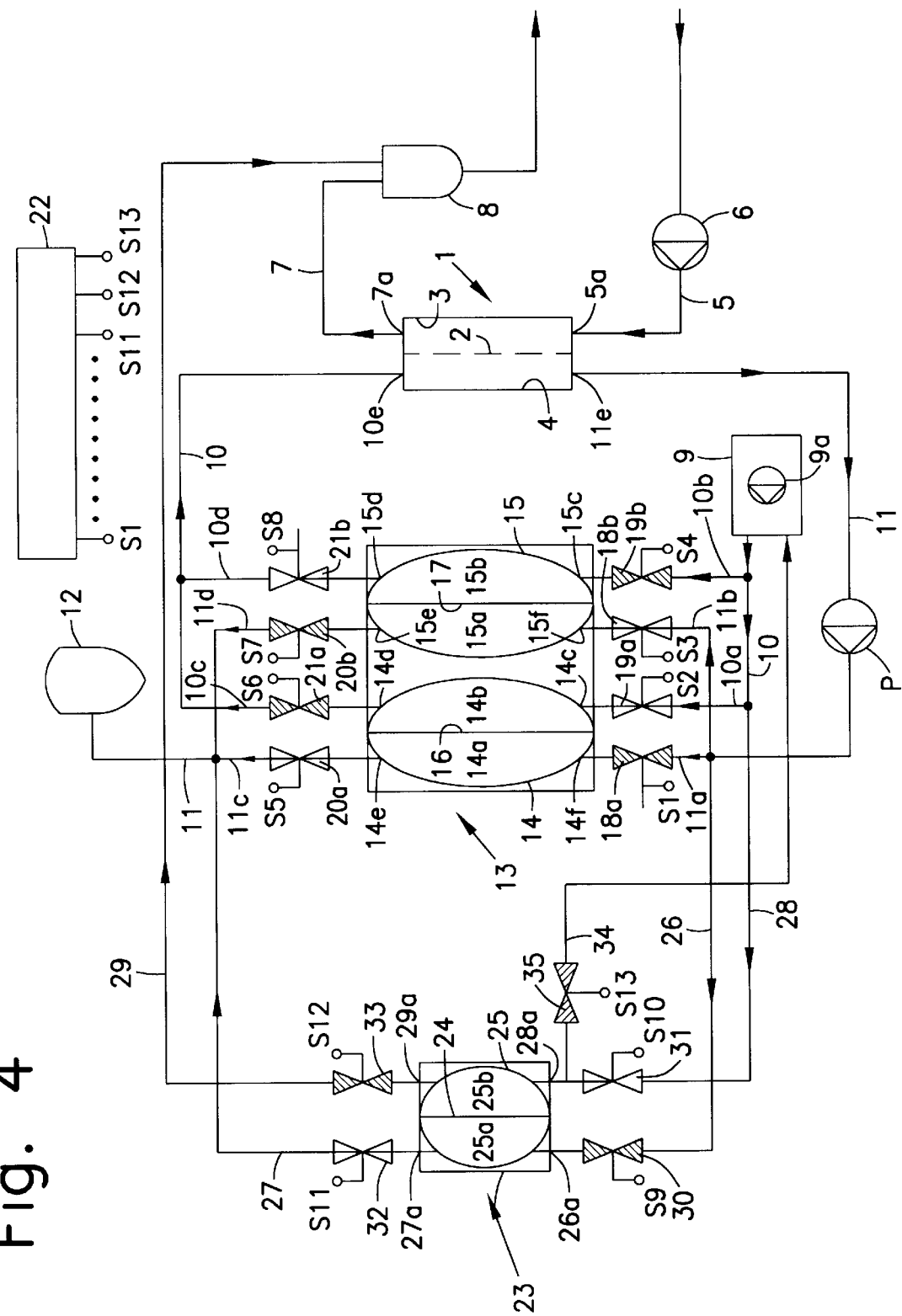
FIG. 4 shows the hemodiafiltration device of FIG. 1 in the substitution mode during a second cycle.

FIGS. 1 and 2 show the switch positions of the valves when the hemodiafiltration device is operated in the so-called ultrafiltration mode. FIGS. 3 and 4 show operation of the hemodiafiltration device in the substitution mode. For the purpose of illustration, the opened valves are shown light in the figures and the closed valves are shown dark.

The ultrafiltration mode is described in detail below with reference to FIGS. 1 and 2.

In a first cycle, valves 18a, 19b, 21a, 20b, 30 and 35 are opened by the central control unit 22, while all the other valves are closed.

Fresh dialysis fluid (30 mL) flows out of dialysis fluid source 9 into the second chamber half 15b of the second balance chamber 15, so that the spent dialysis fluid (30 mL) which was sent into the first chamber half 15a in a preceding cycle is diverted into drain 12. At the same time, spent dialysis fluid (30 mL) is pumped by dialysis fluid pump P out of dialysis fluid chamber 4 of dialyzer 1 and into the first chamber half 14a of the first balance chamber 14, so that fresh dialysis fluid previously sent into the second chamber half 14b is diverted from the second chamber half and sent to dialysis fluid chamber 4.

While balance chambers 14 and 15 of dialysis fluid balancing device 13 are being filled or emptied, the first chamber half 25a of balance chamber 25 of the ultrafiltration balancing device 23 is being filled with spent dialysis fluid (6 mL), so that fresh dialysis fluid which was sent into the second chamber half 25b in a preceding cycle flows back to the dialysis fluid source 9 through drain line 34 while valve 35 is opened. However, drain line 34 can also be connected directly to drain 12.

In a second operating cycle, valves 19a, 18b, 20a, 21b, 31 and 32 are opened, while all the other valves are closed. Fresh dialysis fluid flows into the second chamber half 14b of the first balance chamber 14 of dialysis fluid balancing device 13, so that spent dialysis fluid from the first chamber half 14a is diverted into drain 12. At the same time, spent dialysis fluid is conveyed into the first chamber half 15a of the second balance chamber 15, so that fresh dialysis fluid from the second chamber half 15b is diverted and sent to dialysis fluid chamber 4.

While balance chambers 14 and 15 of dialysis fluid balancing device 13 are being filled or emptied, fresh dialysis fluid (6 mL) is sent into the second chamber half 25b of balance chamber 25 of the ultrafiltration balancing device 23, so that spent dialysis fluid from the first chamber half 25a is diverted into drain 12.

Then valves 18a, 19b, 21a, 20b, 30 and 35 are opened, while all the other valves are closed, so the first cycle can be repeated (FIG. 1).

Removal of fluid takes place in every second cycle, with 3 mL ultrafiltrate, corresponding to one-tenth the dialysate flow, being removed from the dialysis fluid path per balance-chamber cycle.

The substitution mode is described in detail below with reference to FIGS. 3 and 4. The substitution mode differs from the ultrafiltration mode in that the substituate, i.e., the fresh dialysis fluid diverted from the second chamber half 25b of balance chamber 23, is not sent to dialysis fluid source 9 but instead to drip chamber 8.

FIG. 3 shows the switch position of the valves in the first cycle, which corresponds to the first cycle in the ultrafiltration mode (FIG. 1) except that valve 33, which is arranged in substituate outlet line 29, is opened rather than closed, and valve 35 arranged in outlet line 34 is closed instead of being opened, so that the fresh dialysis fluid diverted from the second chamber half 25b can be supplied to the patient again as substituate through outlet line 29, drip chamber 8, and blood outlet line 7. The second cycle in the substitution mode is identical to the second cycle of the ultrafiltration mode. The second cycle is followed by the first cycle again according to the ultrafiltration mode (FIG. 3).

The hemodiafiltration device can also be operated with ultrafiltration balancing device 23 turned off, so that no more ultrafiltration occurs in the corresponding cycles. To do so, valves 30, 31, 32, and 33 are closed in individual cycles or over the entire treatment period.

What is claimed is:

1. A method for ultrafiltration in hemodialysis for use with a dialyzer subdivided by a semipermeable membrane into a blood chamber and a dialysis chamber, a dialysis fluid balancing device having a first dialysis fluid balance chamber subdivided by a moveable partition into a first and a second portion, and an ultrafiltrate balancing device having an ultrafiltrate balance chamber having a first and a second ultrafiltrate balance chamber portion, wherein blood passes in a blood circulation through the blood chamber, wherein dialysis fluid passes through the dialysis fluid chamber in a dialysis fluid path so that a fresh dialysis fluid flows into the dialysis fluid chamber and a spent dialysis fluid flows out of the dialysis fluid chamber, and wherein an ultrafiltrate may be removed from the dialysis fluid path, the method comprising the steps of:

balancing the fresh dialysis fluid and spent dialysis fluid in the dialysis fluid balancing device;

during a first cycle, sending spent dialysis fluid into the first ultrafiltrate balance chamber portion, so that substituate is diverted from the second ultrafiltrate balance chamber portion; and during a second cycle, sending substituate into the second ultrafiltrate balance chamber portion, so that spent dialysis fluid from the first ultrafiltrate balance chamber portion is diverted.

2. The method as recited in claim 1 further comprising the step of adding substituate diverted from the second ultrafiltrate balance chamber portion to the blood circulation.

3. The method as recited in claim 1 wherein the substituate is provided from a source selected from the group consisting essentially of fresh dialysis fluid and an external substituate supply source.

4. The method as recited in claim 1 wherein the dialysis fluid balancing device includes a second dialysis fluid balance chamber having a third portion and a fourth portion and the balancing step includes:

during the first cycle, filling the first portion with spent dialysis fluid, so that fresh dialysis fluid from the second portion is diverted into the dialysis fluid chamber, and filling the fourth portion with fresh dialysis fluid, so that spent dialysis fluid from the third portion is diverted into an outlet; and during the second cycle, filling the second portion with fresh dialysis fluid, so that spent dialysis fluid from the first portion is diverted into the outlet, and filling the third portion with spent dialysis fluid, so fresh dialysis fluid from the fourth portion is diverted into the dialysis fluid chamber.

5. A method for ultrafiltration in hemodialysis for use with an ultrafiltrate balancing device having an ultrafiltrate balance chamber having a first and a second ultrafiltrate balance chamber portion comprising the steps of:

dialyzing blood using a dialyzer, a fresh dialysis fluid entering the dialyzer and a spent dialysis fluid exiting the dialyzer;

balancing the fresh dialysis fluid and the spent dialysis fluid in a dialysis fluid balancing device, the balanced fresh dialysis fluid being sent to the dialyzer;

during a first cycle, sending spent dialysis fluid into the first ultrafiltrate balance chamber portion, so that substituate is diverted from the second ultrafiltrate balance chamber portion;

during a second cycle, sending substituate into the second ultrafiltrate balance chamber portion, so that spent dialysis fluid from the first ultrafiltrate balance chamber portion is removed.

6. The method as recited in claim 5 wherein the diverted substituate is sent to a blood circulation.

7. The method as recited in claim 5 wherein the diverted substituate is returned to a dialysis fluid source.

8. The method as recited in claim 5 wherein a dialysis fluid balancing device includes a first dialysis fluid balance chamber having a first portion and a second portion and a second dialysis fluid balance chamber having a third portion and a fourth portion and the balancing step includes:

during the first cycle, filling the first portion with spent dialysis fluid, so that fresh dialysis fluid from the second portion is diverted into the dialysis fluid chamber, and filling the fourth portion with fresh dialysis fluid, so that spent dialysis fluid from the third portion is diverted into an outlet; and during the second cycle, filling the second portion with fresh dialysis fluid, so that spent dialysis fluid from the first portion is diverted into the outlet, and filling the third portion with spent dialysis fluid, so fresh dialysis fluid from the fourth portion is diverted into the dialysis fluid chamber.

9. An apparatus for ultrafiltration in hemodialysis comprising:

a dialyzer subdivided by a semipermeable membrane into a blood chamber and a dialysis fluid chamber, the blood chamber being part of a blood circulation;

a dialysis fluid source;

an inlet and an outlet line connected to the dialysis fluid chamber, the inlet line supplying a fresh dialysis fluid from the dialysis fluid source into the dialysis fluid chamber and the outlet line removing spent dialysis fluid from the dialysis fluid chamber into a drain;

a dialysis fluid balancing device connected to the inlet and outlet lines for balancing the fresh and spent dialysis fluid, the dialysis fluid balancing device including a balance chamber subdivided into first and second balance chamber portions by a movable partition, with an inlet and an outlet cutoff element arranged in the inlet and the outlet lines connected to the balance chamber portions;

a control unit connected to the inlet and outlet cutoff elements;

a device for removing an ultrafiltrate from the dialysis fluid path; and a substituate source for supplying a substituate;

the device for removing ultrafiltrate including an ultrafiltrate balancing device having an ultrafiltrate balance chamber subdivided by another movable partition into first and second ultrafiltrate chamber portions, wherein the first ultrafiltrate chamber portion is connected by a filtrate inlet line to the dialysis fluid path and by a filtrate outlet line to the drain, and the second ultrafiltrate chamber portion is connected by a substituate inlet line to the substituate source and is also connected to a substituate outlet line;

an ultrafiltrate cutoff element being provided in the ultrafiltrate outlet and ultrafiltrate inlet lines and a substituate cutoff element being provided in the substituate inlet and substituate outlet lines, the control unit connected to the ultrafiltrate and substituate cutoff elements; and the control unit operating during a first cycle so that the first ultrafiltrate chamber portion is filled with ultrafiltrate, so as to divert substituate from the second ultrafiltrate chamber portion, and during a second cycle so that the second ultrafiltrate chamber portion may be filled with substituate, so as to divert ultrafiltrate from the first ultrafiltrate chamber portion into an outlet.

10. The apparatus as recited in claim 9 wherein the substituate outlet line is connected to the blood circulation.

11. The apparatus as recited in claim 9 wherein the substituate source and the dialysis fluid source are a single common supply unit for supplying fresh dialysis fluid.

12. The apparatus as recited in claim 9 further comprising a pump for pumping spent dialysis fluid arranged in the dialysis fluid path.

13. The apparatus as recited in claim 9 wherein the dialysis fluid balancing device includes a second balance chamber connected in parallel to the first balance chamber, and having a third balance chamber portion and a fourth balance chamber portion, the control unit operating so that in the first cycle, the first balance chamber portion can be filled with spent dialysis fluid, so as to divert fresh dialysis fluid from the second chamber portion into the dialysis fluid chamber, and the fourth balance chamber portion can be filled with fresh dialysis fluid, so as to divert spent dialysis fluid from the third balance chamber portion into the outlet, and in the second cycle, the second balance chamber portion can be filled with fresh dialysis fluid, so as to divert spent dialysis fluid from the first balance chamber portion into the outlet, and the third balance chamber portion can be filled with spent dialysis fluid, so as to divert fresh dialysis fluid from the fourth balance chamber portion into the dialysis fluid chamber.

14. The apparatus as recited in claim 9 wherein a filling volume of the ultrafiltrate balance chamber is smaller than a filling volume of the first balance chamber.

15. An apparatus for ultrafiltration in hemodialysis comprising:

a dialysis fluid source;

a dialyzer having an inlet line for supplying a fresh dialysis fluid from the dialysis fluid source and an outlet line for spent dialysis fluid;

a dialysis fluid balancing device connected to the dialyzer for balancing the fresh and spent dialysis fluids; and an ultrafiltrate balancing device having an ultrafiltrate balance chamber subdivided by a movable partition into a first ultrafiltrate chamber portion and a second ultrafiltrate chamber portion, the first ultrafiltrate chamber portion being connected to the outlet line, the second ultrafiltrate chamber portion being connected to the dialysis fluid source and to at least one of a blood circulation and a return line to the dialysis fluid source.

16. The apparatus as recited in claim 15 wherein the second ultrafiltrate chamber portion is connected to the blood circulation.

17. The apparatus as recited in claim 15 wherein the second ultrafiltrate chamber portion is connected to both the blood circulation and the return line.

18. The apparatus as recited in claim 15 further comprising a pump for pumping dialysis fluid.

19. The apparatus as recited in claim 15 wherein the dialysis fluid balancing device includes a first and a second balance chamber connected in parallel.

20. The apparatus as recited in claim 15 wherein a filling volume of the ultrafiltrate balancing device is smaller than a filling volume of the dialysis fluid balancing device.

21. The method of claim 3, wherein the external substituate supply source supplies substituate by means selected from the group consisting of pumping the substituate and conveying the substituate using gravity.

* * * * *